US010319258B2

(12) United States Patent
McClure

(10) Patent No.: US 10,319,258 B2
(45) Date of Patent: Jun. 11, 2019

(54) DENTAL INDIRECT VISION TRAINING APPARATUS

(71) Applicant: Alexander Robert McClure, Malden, MA (US)

(72) Inventor: Alexander Robert McClure, Malden, MA (US)

(*) Notice: Subject to any disclaimer, the term of this patent is extended or adjusted under 35 U.S.C. 154(b) by 236 days.

(21) Appl. No.: 15/637,496

(22) Filed: Jun. 29, 2017

(65) Prior Publication Data

US 2019/0005849 A1 Jan. 3, 2019

(51) Int. Cl.
| G09B 23/28 | (2006.01) |
| A61B 1/247 | (2006.01) |
| G09B 5/02 | (2006.01) |
| G09B 23/34 | (2006.01) |
| A61B 1/24 | (2006.01) |

(52) U.S. Cl.
CPC ............ *G09B 23/283* (2013.01); *A61B 1/247* (2013.01); *G09B 5/02* (2013.01); *G09B 23/34* (2013.01); *A61B 1/24* (2013.01)

(58) Field of Classification Search
USPC ......................... 434/263, 264; 433/53, 54, 57
See application file for complete search history.

(56) References Cited

U.S. PATENT DOCUMENTS

| 1,205,437 | A | * | 11/1916 | Delabarre | ............ | G09B 23/283 |
| | | | | | | 434/264 |
| 1,948,059 | A | | 12/1931 | Baugh | | |
| 3,947,967 | A | | 4/1976 | Satake | | |
| 4,231,181 | A | | 11/1980 | Fabricant | | |
| 4,792,306 | A | * | 12/1988 | Duplantis | ............ | G09B 23/283 |
| | | | | | | 434/264 |
| 4,902,232 | A | | 2/1990 | Neustadter | | |
| 5,120,229 | A | | 6/1992 | Moore et al. | | |
| 5,232,370 | A | | 8/1993 | Hoye | | |
| 5,320,528 | A | * | 6/1994 | Alpern | ................. | A61C 11/001 |
| | | | | | | 433/57 |
| 5,645,425 | A | * | 7/1997 | Callne | .................... | A61C 11/02 |
| | | | | | | 433/54 |
| 5,766,007 | A | * | 6/1998 | Huffman | ................ | A61C 11/02 |
| | | | | | | 433/54 |
| 7,544,061 | B2 | * | 6/2009 | Poitras | ................ | G09B 23/283 |
| | | | | | | 434/263 |
| 7,713,063 | B2 | | 5/2010 | Lee et al. | | |

(Continued)

*Primary Examiner* — Kurt Fernstrom
(74) *Attorney, Agent, or Firm* — Williams Intellectual Property; Benjamin F. Williams

(57) ABSTRACT

A dental indirect vision training apparatus is provided devised to assist in the development of indirect vision eye-hand coordination among dental students. A prosthetic jaw member is rotatably positioned upon a base stand and each of a maxillary and mandibular denture is attachable into the jaw member in positions appropriate to resemble human anatomy. Target members disposed upon each of the maxillary and mandibular teeth enable practiced movements with dental tools wielded to contact the target members by indirect sighting via a manually coordinated dental mirror. Dental students thereby learn spatial relationships and eye-hand coordination interior to an oral cavity while visually apprehending images reflected at angles atypically experienced in everyday life. Indirect vision and coordinated movements are thereby explored, strengthened, and developed.

9 Claims, 5 Drawing Sheets

(56) References Cited

U.S. PATENT DOCUMENTS

| | | | | |
|---|---|---|---|---|
| 8,235,727 B2* | 8/2012 | Lee | .................. | A61C 11/022 |
| | | | | 434/263 |
| 8,376,753 B2 | 2/2013 | Riener et al. | | |
| 8,641,422 B2 | 2/2014 | Francavilla | | |
| 2004/0091845 A1 | 5/2004 | Azerad et al. | | |
| 2008/0220404 A1* | 9/2008 | Woidschutzke | ..... | A61C 11/022 |
| | | | | 434/263 |
| 2012/0122065 A1* | 5/2012 | Snoad | .................. | G09B 23/283 |
| | | | | 434/263 |

* cited by examiner

DENTAL INDIRECT VISION TRAINING APPARATUS

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of dental aids are known in the prior art. Most are exemplary visual aids used to demonstrate the local position of various portions of human anatomy for the purposes of discussion and presentation. None are devised to assist in experientially developing the skill of indirect vision required to successfully coordinate a dental mirror and a dental tool in concert interior to an oral cavity. Learning indirect vision, as required to properly coordinate eye-hand movements through reflected images within an oral cavity, can be difficult and confusing. What is needed is a dental indirect vision training apparatus that presents a prosthetic jaw member moveable through a plurality of orientations to present each of a maxillary and mandibular denture in a variety of spatial situations, whereon a user may practice engaging a dental tool against particular target members disposed upon the maxillary and mandibular teeth, for view in a dental mirror and target by a dental tool, whereby eye-hand movements may be coordinated and indirect vision practiced previous to effecting procedure upon a living patient.

FIELD OF THE INVENTION

The present invention relates to a dental indirect vision training apparatus devised to assist dental students in developing indirect vision when performing procedures in an oral cavity. Visioning interior the oral cavity is enabled by manual action to correctly orient a dental mirror and reveal portions of teeth and gums otherwise obstructed and occluded therein. Such indirect vision—that is, determination of space through images reflected in a mirror—is confusing and difficult to master. The present invention enables use of interchangeable maxillary and mandibular dentures, securable into a prosthetic jaw member, to practice engagement of dental tools against target members disposed upon each of the maxillary and mandibular teeth, whereby use of the dental mirror and an associated dental tool (such as a dental drill or pick, for example) assists development of eye-hand coordination and indirect vision through a series of actions required to engage each of the target members.

SUMMARY OF THE INVENTION

The present dental indirect vision training apparatus has been devised to assist in developing eye-hand coordination via indirect vision of teeth viewed through the agency of a dental mirror. The present dental indirect vision apparatus presents an interchangeable maxillary denture and an interchangeable mandibular denture upon which various target members are disposed for interaction with a dental tool wielded in the hands of a user. Each of the maxillary and mandibular dentures are attachable into each of a respective maxillary seat member and a mandibular seat member disposed upon a prosthetic jaw member, whereby a user may practice indirect vision by sighting the target members and engaging a replica dental tool thereagainst, as will be described subsequently. Since movements of the hands operating in an oral cavity are rendered visible in a handheld dental mirror, eye-hand coordination is often confusable when learning dental procedures. The present apparatus, therefore, enables a user to practice indirect visioning of teeth and learn to develop eye-hand coordination previous to work with actual patients.

The present indirect vision training apparatus, therefore, includes a prosthetic jaw member rotatably attached to a base stand. The prosthetic jaw member need not actually resemble a real jaw per se. The prosthetic jaw member presents an opening approximate to an oral cavity of average dimensions and includes each of a maxillary seat member and a mandibular seat member in appropriate position relative a human jaw and devised to attachably house each of an associated maxillary denture and a mandibular denture respectively in appropriate position simulative of human anatomy.

The base stand may include a weighted portion to extend a low center of mass over an underlying surface to resist toppling and displacement. In some embodiments securement members, such as suction cups for example, may be employed to secure the base stand to an underlying surface. The base stand includes an apex whereat the prosthetic jaw is rotatably disposed. The jaw member may be rotatable around a horizontal axis of rotation through 360° and also around a vertical axis of rotation through 360°. Importantly, the jaw member is rotatably positionable and securable into a variety of orientations to require use of a handheld dental mirror to maintain line of sight to the cusps of the maxillary and mandibular teeth, as case may be.

A maxillary denture is attachable into the maxillary seat member. The maxillary denture includes a plurality of maxillary teeth devised to resemble human teeth. A variety of maxillary dentures is contemplated for use with the device, interchangeably attachable to the maxillary seat member, such as, for example, a maxillary denture resembling adult teeth, a maxillary denture resembling juvenile teeth, among other potential embodiments appreciable to a person having ordinary skill in the art.

A mandibular denture is likewise attachable into the mandibular seat member. The mandibular denture likewise includes a plurality of mandibular teeth devised to resemble human teeth. A variety of mandibular dentures is likewise contemplated for use with the present device, interchangeably attachable to the mandibular seat member, such as, for example, a mandibular denture resembling adult teeth, a mandibular denture resembling juvenile teeth, among other potential embodiments appreciable to a person having ordinary skill in the art.

A target member is disposed upon the occlusal surface of at least one of the plurality of maxillary teeth and upon the occlusal surface of at least one of the mandibular teeth. The target member is devised for particular contact with a dental tool, as will be described subsequently, whereby indirect vision enabled by manual action holding the dental mirror is developed. In one embodiment of the present apparatus, the target member includes indicia disposed upon the cusp and grooves of each tooth. The indicia includes at least one line, demarked upon the tooth surface, whereby a user may practice indirect vision by tracing engagement of a dental pick along the extent of the at least one line. Indicia may likewise be disposed on additional parts of teeth, for example upon the side of the tooth, say.

In another embodiment the target member includes a recess cut into each tooth, said recess devised for fitting engagement with a replica dental drill having a replica drill bit disposed therein of similar dimensions as an actual dental drill bit. In this embodiment the replica drill bit may interact with the tooth, for example to color the tooth where the bit contacts the tooth, whereby a user may review said user's attempts to fit the replica drill bit into the recess and discern false impacts made outside the particular target member the user aimed to meet. Further, the recess may delimit an interior surface therein whereby manual action of the replica drill interior to the recess may enable coloring of the interior surface whereby a user may determine said user's scope of contact applied within the recess.

A user may, therefore, fit a particular maxillary denture into the maxillary seat member in the jaw member to practice indirect vision therewith by tracing engagement of a dental pick along the extent of at least one line of indicia comprising the target member. A user may thus interchange the maxillary denture with another maxillary denture, for example, to practice on juvenile teeth, deciduous teeth, even abnormal teeth, or to practice fitting the replica drill into each recess comprising the target member in such an embodiment. The user may likewise interchange the mandibular denture to mix and match or replace embodiments as desired. The user may rotate the jaw member through multiple orientations to further practice indirect vision of the target members and manual interaction therewith with each of a plurality of dental tools. Thus indirect vision may by developed previous to work on an actual patient to increase the skill and competency of dental students previous to work on actual dental procedures.

Thus has been broadly outlined the more important features of the present dental indirect vision training apparatus so that the detailed description thereof that follows may be better understood and in order that the present contribution to the art may be better appreciated.

Objects of the present dental indirect vision training apparatus, along with various novel features that characterize the invention are particularly pointed out in the claims forming a part of this disclosure. For better understanding of the dental indirect vision training apparatus, its operating advantages and specific objects attained by its uses, refer to the accompanying drawings and description.

BRIEF DESCRIPTION OF THE DRAWINGS

Figures

DETAILED DESCRIPTION OF THE DRAWINGS

Figure 1:
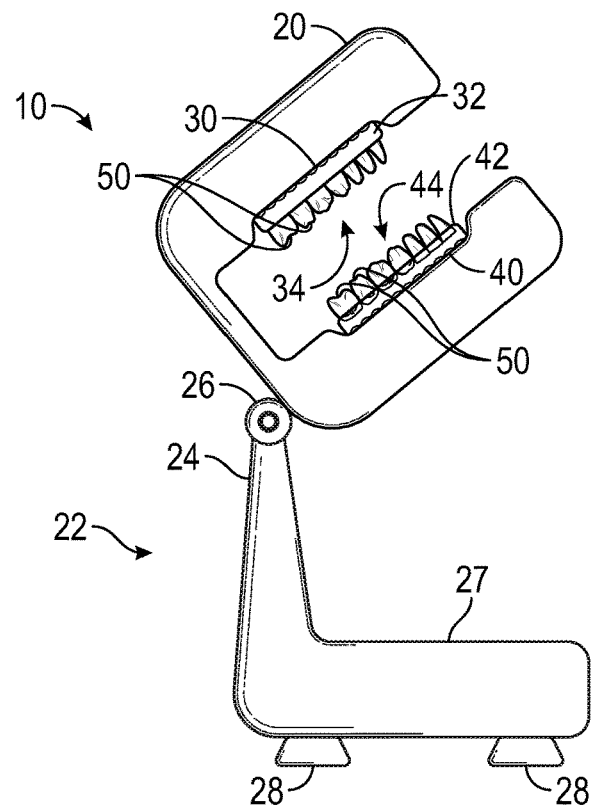
FIG. 1 is a side view of an example embodiment.
Figure 2:
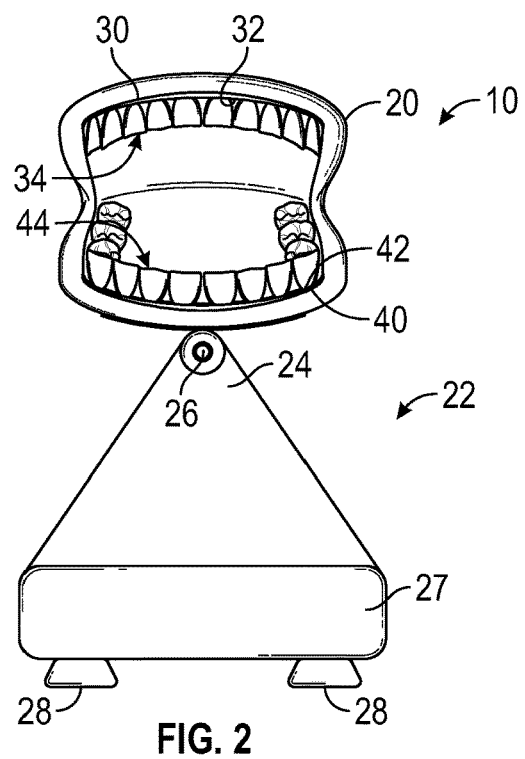
FIG. 2 is a front view of an example embodiment.
Figure 3:
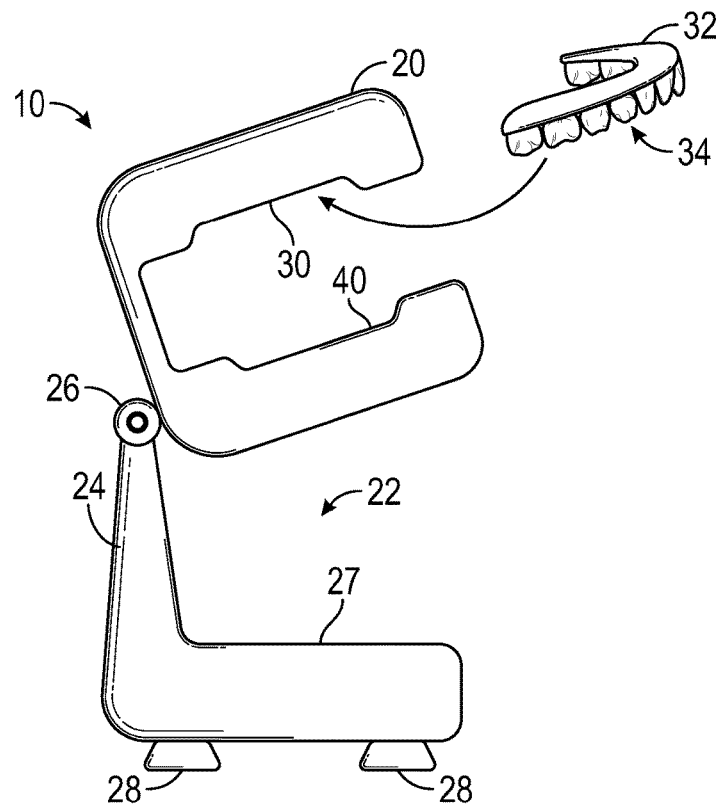
FIG. 3 is a side view of an example embodiment with a maxillary denture detached from a maxillary seat member.
Figure 4:
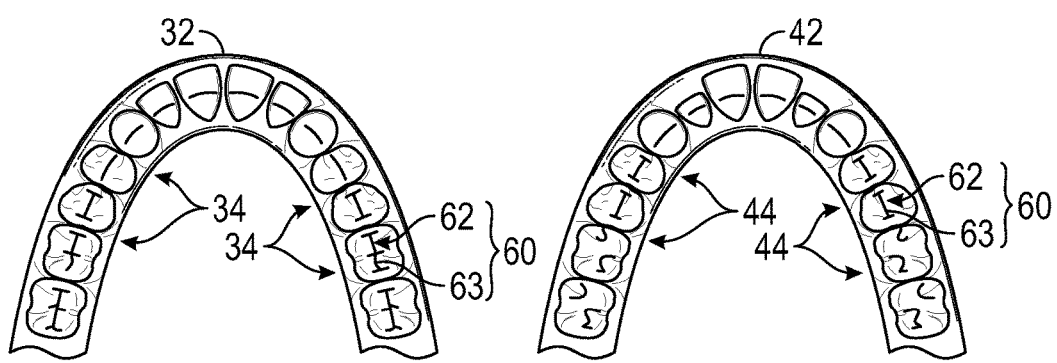
FIG. 4 is an elevation view of a maxillary denture and a mandibular denture showing target members comprising indicia disposed upon each occlusal surface of each of a plurality of maxillary teeth and each of a plurality of mandibular teeth.
Figure 5:
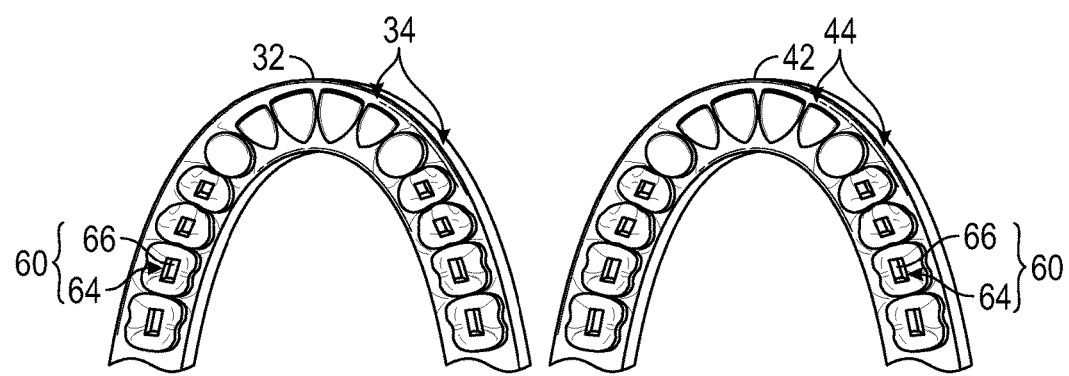
FIG. 5 is an elevation view of a maxillary denture and a mandibular denture showing target members comprising a recess disposed upon the occlusal surface of premolars and molars of a plurality of maxillary teeth and premolars and molars of a plurality of mandibular teeth.
Figure 6:
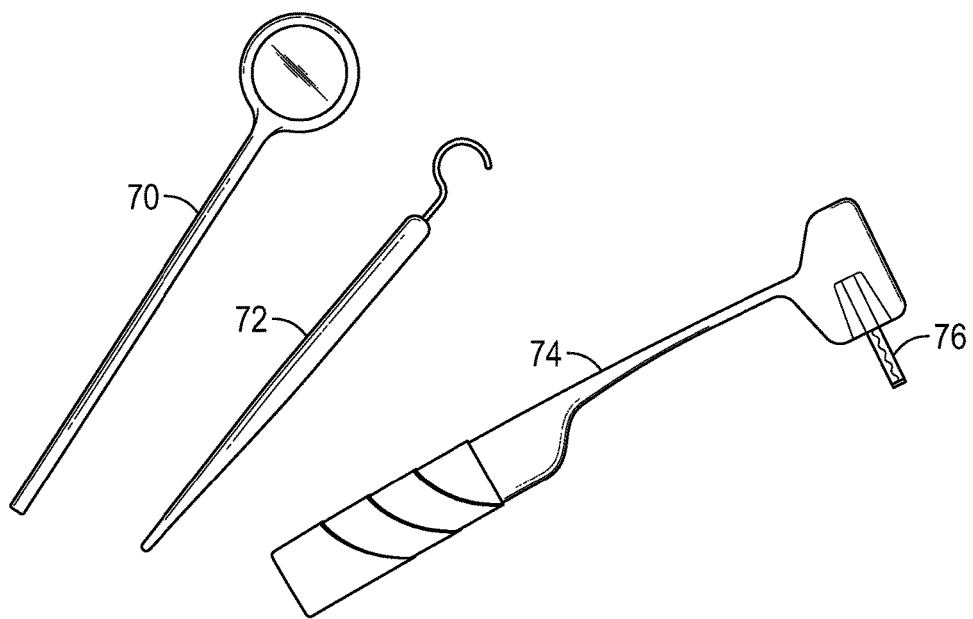
FIG. 6 is an elevation view of a plurality of dental tools.
Figure 7:
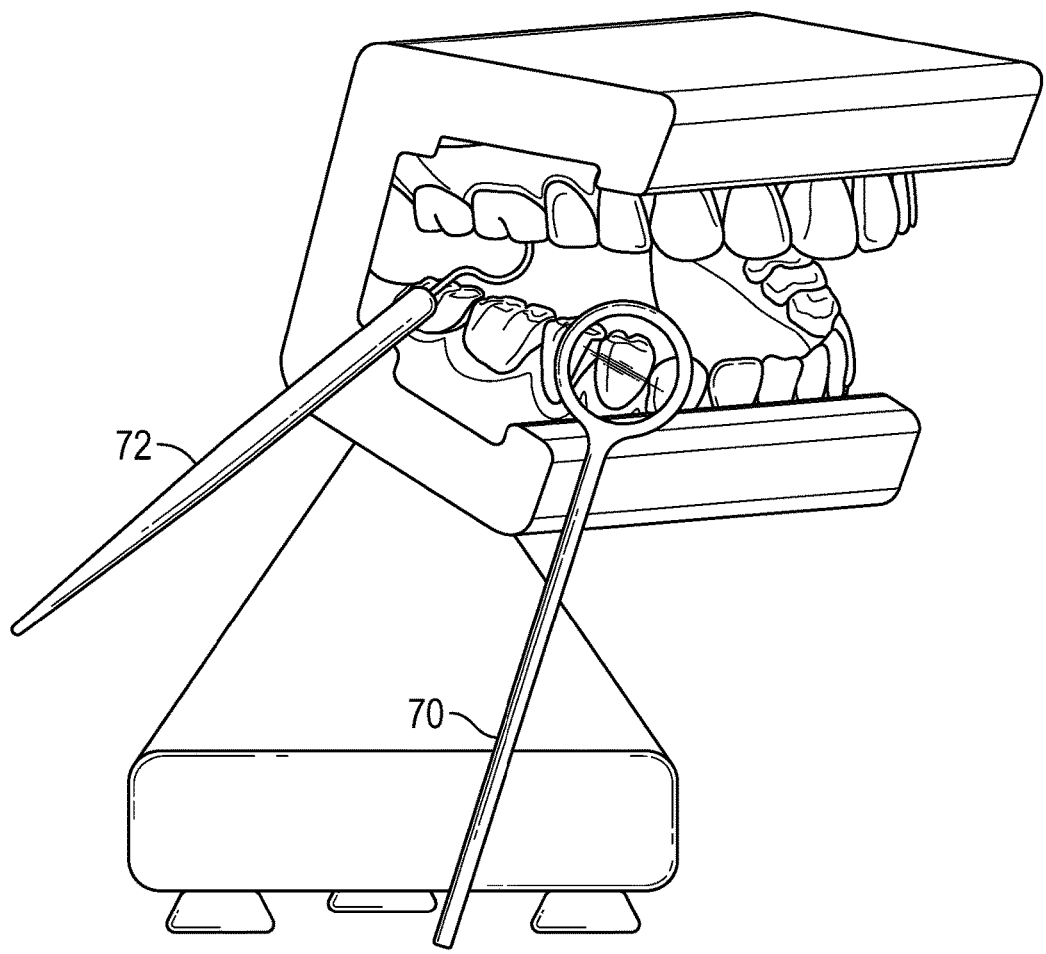
FIG. 7 is an in-use view showing tracing engagement with a dental pick along at least one line comprising indicia of a target member.
Figure 8:
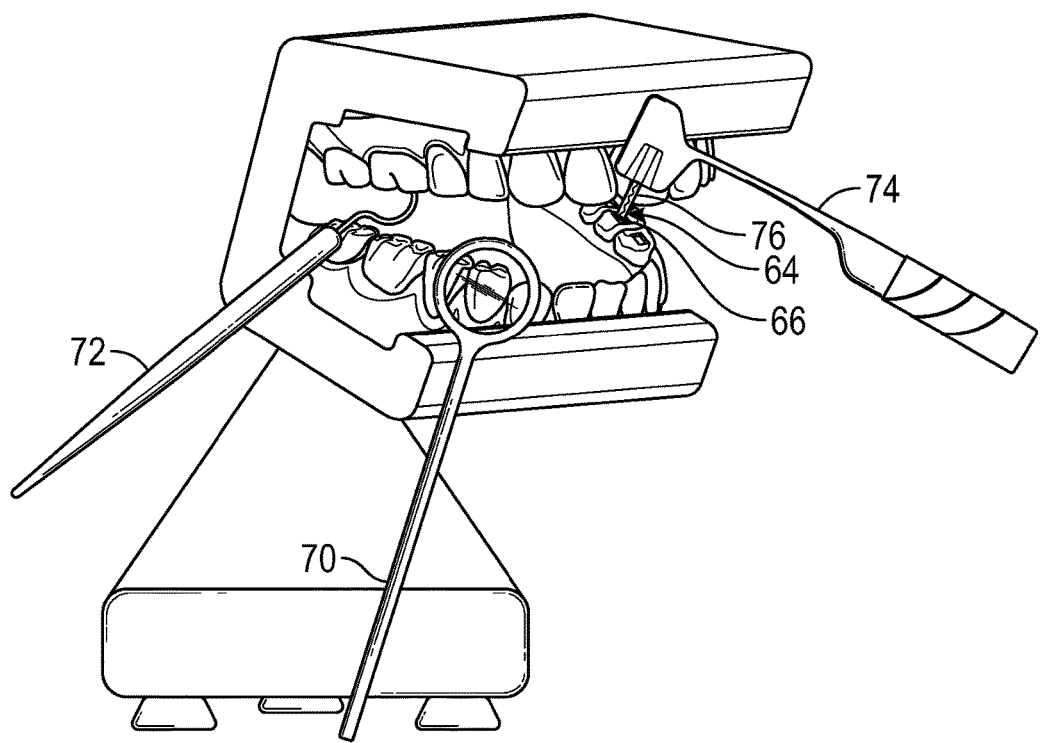
FIG. 8 is an in-use view showing fitting engagement of a replica drill bit into a target member comprising a recess in the cusp of a targeted tooth.

With reference now to the drawings, and in particular FIGS. 1 through 8 thereof, example of the instant dental indirect vision training apparatus employing the principles and concepts of the present dental indirect vision training apparatus and generally designated by the reference number 10 will be described.

Referring to FIGS. 1 through 8 a preferred embodiment of the present dental indirect vision training apparatus 10 is illustrated.

The present dental indirect vision training apparatus 10 has been devised to assist in the development of indirect vision eye-hand coordination required by dentists when conducting procedures interior to the oral cavity of any patient. The present dental indirect vision training apparatus 10, therefore, includes a prosthetic jaw member 20 rotatably disposed upon a base stand 22. The jaw member 20 includes a maxillary seat member 30 and a mandibular seat member 40 devised to attach an interchangeable maxillary denture 32 and an interchangeable mandibular denture 42, respectively.

The base stand 22 includes an apex 24 having a rotatable member 26 connectable to the jaw member 20. The jaw member 20 is thus positionable through a filed of rotation to present the prosthetic oral cavity in a plurality of orientations suited for developing indirect vision techniques when working with an obstructed line of sight, as will be described subsequently. In the example embodiment depicted, the rotatable member is rotatable through 360° about a horizontal plane and through 360° about a vertical plane. The base stand 22 may have a weighted portion 27 with a low center of mass or include securement members 28 whereby the base stand 22 is securable to an underlying surface. In the example embodiment shown the securement members are suction cups.

The maxillary denture 32 has a plurality of maxillary teeth 34 thereupon, said maxillary teeth 34 devised to resemble the maxillary teeth of a human patient. For example, the plurality of maxillary teeth 34 may include a central incisor, lateral incisor, canine (cuspid), first premolar (first bicuspid), second premolar (second bicuspid), first molar, second molar, and a third molar in both dexter and sinister series.

The mandibular denture 42 has a plurality of mandibular teeth 44 thereupon, said mandibular teeth 44 devised to resemble the mandibular teeth of a human patient. For example, the plurality of mandibular teeth 44 may include a central incisor, lateral incisor, canine (cuspid), first premolar (first bicuspid), second premolar (second bicuspid), first molar, second molar, and a third molar in both dexter and sinister series. Additional embodiments are contemplated for younger patients with deciduous teeth (e.g. a central incisor, lateral incisor, canine, and first and second molars of a lesser size) as well as abnormal teeth, for example.

An occlusal surface 50 is disposed atop each of the plurality of maxillary teeth 34 and atop each of the mandibular teeth 44 (the term "occlusal surface", as used herein, is taken to include any apical surface cresting an uppermost reach of a tooth and any corrugated surface that would apply force to food matter during mastication). To assist in eye-hand coordination while employing indirect vision by manual action of a dental mirror 70 positioned in simulation of an appropriate position in an oral cavity of an actual patient, a target member 60 is disposed upon each occlusal surface 50. The target member 60 is configured for contact with a dental tool 72, 74 manually wielded and indirectly sighted by a user indirectly visioning each occlusal surface 50 via manually wielding the dental mirror 70 to maintain line of sight with the occlusal surface 50 of any particularly targeted tooth.

The target member 60 includes indicia 62 having at least one line 63 demarked upon each respective occlusal surface 50. The at least one line 63 is demarked in contrasting pigment relative the occlusal surface 50 for visual apprehension in the dental mirror 70. A user thereby improves eye-hand coordination via indirect vision by repeatedly tracing along the indicia 62 with a dental pick 72 wielded by a user in a hand not holding the dental mirror 70.

The target member 60, in another embodiment, includes a recess 64 into the occlusal surface 50 of each respective tooth. The recess 64 is devised for insertable and fitting engagement with a replica dental drill 72. The replica dental drill 74 includes a replica drill bit 76 devised to interact with the interior of each tooth to signal contact with an interior surface 66 thereof. In the example embodiment disclosed herein, the replica drill bit 76 is contemplated to comprise a cylindrical portion of graphite whereby contact with the interior surface 66 delimiting the recess 64 renders coloration thereto, whereby a user is enabled to determine the extent of contact with the interior surface 66 of each targeted tooth. Further, contact made to other parts of the particular denture being targeted may likewise by signaled by coloration outside the targeted recess.

Thus contacting the target member 60 upon each cusp 50 of each of the plurality of maxillary and mandibular teeth 34, 44 assists a user in developing indirect vision and the associated eye-hand coordination required when conducting dental procedures in a patient's mouth.

What is claimed is:

1. A dental indirect vision training apparatus comprising:
   an interchangeable maxillary denture moveably attachable at a base stand, said maxillary denture having a plurality of maxillary teeth thereupon;
   an interchangeable mandibular denture attachable moveably at the base stand, said mandibular denture having a plurality of mandibular teeth thereupon; and
   a target member disposed upon at least one of the plurality of maxillary teeth and at least one of the plurality of mandibular teeth, said target member configured for indirect sighting and subsequent contact with a dental tool manually wielded by a user indirectly visioning each of said teeth via a dental mirror;
   wherein contacting each target member upon each of the plurality of maxillary and mandibular teeth assists in developing indirect vision and associated eye-hand coordination.

2. The dental indirect vision training apparatus of claim 1 wherein the target member comprises indicia having at least one line demarked for tracing engagement with a dental pick whereby a user develops indirect vision as a result of tracing the extent of said at least one line.

3. The dental indirect vision training apparatus of claim 1 wherein the target member comprises a recess disposed upon an occlusal surface of at least one of the plurality of maxillary and mandibular teeth, said recess devised for insertable and fitting engagement with a replica dental drill, said replica dental drill having a replica drill bit devised to signal contact with an interior surface of the recess whereby a user develops indirect vision as a result of inserting the replica drill bit into targeted recess.

4. The dental indirect vision training apparatus of claim 2 wherein the indicia is colored in a contrasting pigment relative each tooth cusp for visual apprehension of the user.

5. The dental indirect vision training apparatus of claim 3 wherein the drill bit is configured to color the interior surface of the recess whereby the user is apprised of the position the drill bit took across the interior surface of the recess into which the drill bit was inserted.

6. The dental indirect vision training apparatus of claim 5 wherein the drill bit consists of graphite.

7. A dental indirect vision training apparatus comprising:
   a prosthetic jaw member rotatably disposed upon a base stand;
   a maxillary seat member disposed upon the jaw member;
   a mandibular seat member disposed upon the jaw member;
   an interchangeable maxillary denture attachable to the maxillary seat member, said maxillary denture having a plurality of maxillary teeth thereupon;
   an interchangeable mandibular denture attachable to the mandibular seat member, said mandibular denture having a plurality of mandibular teeth thereupon;
   an occlusal surface disposed atop each of the plurality of maxillary teeth and atop each of the mandibular teeth;
   a target member disposed upon each said occlusal surface, said target member configured for contact with a dental tool manually wielded and indirectly sighted by a user indirectly visioning each occlusal surface via a dental mirror oriented proximal said occlusal surface, said target member comprising:
      indicia having at least one line demarked upon the occlusal surface, said at least one line demarked in contrasting pigment relative the occlusal surface for visual apprehension in a dental mirror and tracing engagement with a dental pick wielded by a user; and
      a recess disposed into the occlusal surface devised for insertable and fitting engagement with a replica dental drill, said replica dental drill having a replica drill bit devised to interact with the interior of each tooth to signal contact with an interior surface thereof;
   wherein contacting the target member upon each occlusal surface of each of the plurality of maxillary and mandibular teeth assists in developing indirect vision.

8. The dental indirect vision training apparatus of claim 7 wherein the drill bit is configured to color the interior surface of the recess whereby the user is apprised of the position the drill bit took across the interior surface of the recess into which the drill bit was inserted.

9. The dental indirect vision training apparatus of claim 8 wherein the drill bit consists of graphite.

* * * * *